US008598408B2

(12) United States Patent
Satofuka et al.

(10) Patent No.: US 8,598,408 B2
(45) Date of Patent: *Dec. 3, 2013

(54) METHOD OF PRODUCING AN ANTIBODY USING A CANCER CELL

(75) Inventors: Hiroyuki Satofuka, Chiba (JP); Masahiro Uchino, Chiba (JP); Shingo Hanaoka, Chiba (JP)

(73) Assignee: Ordermade Medical Research Inc., Nagareyama-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/378,956

(22) PCT Filed: Aug. 24, 2011

(86) PCT No.: PCT/JP2011/069678
§ 371 (c)(1),
(2), (4) Date: Dec. 16, 2011

(87) PCT Pub. No.: WO2012/026615
PCT Pub. Date: Mar. 1, 2012

(65) Prior Publication Data
US 2012/0151611 A1 Jun. 14, 2012

(30) Foreign Application Priority Data
Aug. 25, 2010 (JP) ................. 2010-188390

(51) Int. Cl.
C12P 21/00 (2006.01)
C12P 21/04 (2006.01)

(52) U.S. Cl.
USPC .......................... 800/6; 435/70.21

(58) Field of Classification Search
USPC .......................... 800/6; 435/70.21
See application file for complete search history.

(56) References Cited

U.S. PATENT DOCUMENTS

| | | | |
|---|---|---|---|
| 2004/0141913 | A1 | 7/2004 | Young et al. |
| 2008/0187537 | A1 | 8/2008 | Tsuchiya et al. |
| 2011/0318387 | A1 | 12/2011 | Satofuka et al. |

FOREIGN PATENT DOCUMENTS

| | | |
|---|---|---|
| EP | 0280209 A2 | 8/1988 |
| EP | 0 761 687 A1 | 3/1997 |
| JP | 64-29400 A | 1/1989 |
| JP | 6-327491 A | 11/1994 |
| JP | 7-188056 A | 7/1995 |
| JP | 7-313187 A | 12/1995 |
| JP | 2000-500653 A | 1/2000 |
| JP | 2001-10974 A | 1/2001 |
| JP | 2001-520011 A | 10/2001 |
| JP | 2004-517885 A | 6/2004 |
| WO | WO 94/11026 A2 | 5/1994 |
| WO | WO 97/18300 A2 | 5/1997 |
| WO | WO 99/19479 A1 | 4/1999 |
| WO | WO 02/057741 A2 | 7/2002 |
| WO | WO 2004/056847 A2 | 7/2004 |
| WO | WO 2005/111208 A1 | 11/2005 |
| WO | WO 2006/109533 A1 | 10/2006 |
| WO | WO 2010/098471 A1 | 9/2010 |

OTHER PUBLICATIONS

Translation of WO/2010/098471. Satofuka et al. See printout from http://patentscope.wipo.int/search/en/detail.jsf?docId=WO2010098471&recNum=1&doc, dated Dec. 12, 2012. pp. 1-13.*
Extended European Search Report for corresponding Application No. 11791414.3 dated Mar. 27, 2013.
Ohno et al., "Production and characterization of highly tumor-specific rat monoclonal antibodies recognizing the extracellular domain of human L-type amino-acid transporter 1", Cancer Science, vol. 99, No. 5, May 2008, pp. 1000-1007, XP002475425.
Antibodies: A Laboratory Manual (1998), Chapter 5, pp. 114-115.
Bast Jr. et al., "Reactivity of a Monoclonal Antibody with Human Ovarian Carcinoma," J. Cin. Invest. (Nov. 1981), vol. 68, pp. 1331-1337.
Drewinko et al., "New Monoclonal Antibodies against Colon Cancer-associated Antigens," Cancer Res (1986), vol. 46, pp. 5137-5143.
Herlyn et al., "Colorectal carcinoma-specific antigen: Detection by means of monoclonal antibodies," Proc. Natl. Acad. Sci. USA (Mar. 1979), vol. 76, No. 3, pp. 1438-1442.
International Search Report mailed Nov. 29, 2011, in PCT International Application No. PCT/JP2011/069678.
Kawanishi, "Antibody Drugs: The Present Status and Perspectives," Folia Pharmacol. Jpn., (2008), vol. 131, pp. 102-108, with English translation.
Kobayashi, "Antibody Preparation by DNA Immunization; Problems Associated with DNA Immunization," Seibutsu Kogaku (Biotechnology) (2008), vol. 86, pp. 384-388, with English translation.
Kojima et al., "Establishment and Analysis of Highly Metastatic Cell Line MCF7-14 . . . ," Dai 30 Kai Annual Meeting of the Molecular Biology Society of Japan, Dai 80 Kai Annual Meeting of the Japanese Biochemical Society Godo Taikai Koen Yoshishu (2007), p. 829 (4P-0927), with English translation.
Koprowski et al., "Colorectal Carcinoma Antigens Detected by Hybridoma Antibodies," Somatic Cell Genetics (1979), vol. 5, No. 6, pp. 957-972.
Metzgar et al., "Antigens of Human Pancreatic Adenocarcinoma Cells Defined by Murine Monoclonal Antibodies," Cancer Res (1982), vol. 42, pp. 601-608.
Saitoh et al., "Viral envelope protein gp64 transgenic mouse facilitates the generation of monclonal antibodies against exogenous membrane proteins displayed on baculovirus," Journal of Immunological Methods (2007), vol. 322, pp. 104-107.

* cited by examiner

*Primary Examiner* — Marcia S Noble
(74) *Attorney, Agent, or Firm* — Birch, Stewart, Kolasch & Birch, LLP

(57) ABSTRACT

The present invention aims to provide a method for antibody preparation. The present invention is directed to a method for preparing an antibody-producing cell, which comprises the following steps:
(1) transplanting metastatic cancer cells capable of expressing a target antigen into a non-human animal to ensure engraftment of the cancer cells in the animal;
(2) immunizing the animal with the target antigen; and
(3) collecting the antibody-producing cell from the immunized animal;
as well as a method for preparing an antibody, which comprises collecting the antibody from the antibody-producing cell prepared by the above method.

13 Claims, 8 Drawing Sheets

A

PCR amplification

H Chain → ← L Chain

B

SDS-PAGE 1   2

1 : crude extract
2 : affinity purified

← scFv

```
                              SEQUENCE LISTING

<160> NUMBER OF SEQ ID NOS: 10

<210> SEQ ID NO 1
<211> LENGTH: 34
<212> TYPE: DNA
<213> ORGANISM: Artificial
<220> FEATURE:
<223> OTHER INFORMATION: Synthetic DNA

<400> SEQUENCE: 1
tgaggagacg gtgaccgtgg tcccttggcc ccag                                 34

<210> SEQ ID NO 2
<211> LENGTH: 22
<212> TYPE: DNA
<213> ORGANISM: Artificial
<220> FEATURE:
<223> OTHER INFORMATION: Synthetic DNA

<400> SEQUENCE: 2
aggtsmarct gcagsagtcw gg                                              22

<210> SEQ ID NO 3
<211> LENGTH: 22
<212> TYPE: DNA
<213> ORGANISM: Artificial
<220> FEATURE:
<223> OTHER INFORMATION: Synthetic DNA

<400> SEQUENCE: 3
gttagatctc cagcttggtc cc                                              22

<210> SEQ ID NO 4
<211> LENGTH: 24
<212> TYPE: DNA
<213> ORGANISM: Artificial
<220> FEATURE:
<223> OTHER INFORMATION: Synthetic DNA

<400> SEQUENCE: 4
gacattcagc tgacccagtc tcca                                            24
```

```
<210> SEQ ID NO 5
<211> LENGTH: 32
<212> TYPE: DNA
<213> ORGANISM: Artificial
<220> FEATURE:
<223> OTHER INFORMATION: Synthetic DNA

<400> SEQUENCE: 5
gcggccatgg ccgtgcaact gcagcagtca gg                                   32

<210> SEQ ID NO 6
<211> LENGTH: 74
<212> TYPE: DNA
<213> ORGANISM: Artificial
<220> FEATURE:
<223> OTHER INFORMATION: Synthetic DNA

<400> SEQUENCE: 6
gtcgtcgacc gatccgccac cgccagagcc acctccgcct gaaccgcctc cacctgagga    60
gacggtgacc gtgg                                                       74

<210> SEQ ID NO 7
<211> LENGTH: 28
<212> TYPE: DNA
<213> ORGANISM: Artificial
<220> FEATURE:
<223> OTHER INFORMATION: Synthetic DNA

<400> SEQUENCE: 7
cggtcgacga cattcagctg acccagtc                                        28

<210> SEQ ID NO 8
<211> LENGTH: 30
<212> TYPE: DNA
<213> ORGANISM: Artificial
<220> FEATURE:
<223> OTHER INFORMATION: Synthetic DNA

<400> SEQUENCE: 8
ccgctcgagc gatctccagc ttggtcccag                                      30

<210> SEQ ID NO 9
<211> LENGTH: 17
<212> TYPE: PRT
<213> ORGANISM: Artificial
<220> FEATURE:
<223> OTHER INFORMATION: Synthetic peptide

<400> SEQUENCE: 9

Ser Ser Gly Gly Gly Gly Ser Gly Gly Gly Gly Ser Gly Gly Gly Gly
1               5                   10                  15

Ser

<210> SEQ ID NO 10
<211> LENGTH: 6
<212> TYPE: PRT
<213> ORGANISM: Artificial
<220> FEATURE:
<223> OTHER INFORMATION: Synthetic peptide

<400> SEQUENCE: 10

His His His His His His
1               5
```

METHOD OF PRODUCING AN ANTIBODY USING A CANCER CELL

TECHNICAL FIELD

The present invention relates to a method for antibody preparation using cancer cells.

BACKGROUND ART

Since polyclonal and monoclonal antibodies have the ability to specifically bind to trace proteins contained in a mixed solution such as blood, they are industrially useful materials as reagents in researches and/or clinical tests or as pharmaceutical preparations, etc.

Antibody molecules strongly induce antigen-antibody reaction against antigens expressed on the cell membrane, and hence desired antibodies are those recognizing membrane proteins in order to expect a therapeutic effect when administered to diseased patients.

Antibodies which have been marketed for use in disease treatment are mostly monoclonal antibodies recognizing membrane proteins (Non-patent Document 1), and they produce a therapeutic effect through their actions such as (1) binding to a target cell to induce cell death directly or indirectly (Patent Document 1) or (2) inhibition of ligand binding to membrane receptors to reduce intracellular signaling (Patent Document 2), etc.

Moreover, antibodies which have been marketed are each obtained as a result of repeating inventive efforts and enormous works.

Various attempts have been made to develop techniques for obtaining antibodies recognizing membrane proteins. However, no simple method has been established for preparation of monoclonal antibodies against membrane proteins.

For example, there is a known method in which a peptide sequence exposed on the cell membrane surface is prepared by forced expression in *E. coli* or other cells or by chemical synthesis, and the peptide sequence thus prepared is attached to a carrier protein to thereby induce immune responses.

However, such a method fails to cause three-dimensional structure formation and/or post-translational modifications (e.g., with sugar chains), and hence it is difficult to yield antibodies recognizing the inherent structure of membrane proteins.

To obtain monoclonal antibodies against membrane proteins, the membrane proteins should retain their inherent three-dimensional structure during immunization into laboratory animals. However, when a surfactant is used for extraction of membrane proteins from the cell membrane, the membrane proteins lose their three-dimensional structure. Or alternatively, when no surfactant is used for this purpose, the membrane proteins aggregate through their hydrophobic regions. Because of these problems, it is not easy to prepare membrane proteins retaining their three-dimensional structure for use as antigens.

As an immunization method using a full-length protein, a genetic immunization method is reported, in which a DNA vector for expression is directly introduced into mice (Patent Document 3). This method has many advantages, particularly in that it requires no purified antigen and in that it yields antibodies recognizing the three-dimensional structure of a target molecule.

However, such a method is known to have problems to be solved, for example, in that (1) the transgene should be expressed on the cell surface in order to induce immune responses, (2) sufficient immunization cannot be achieved due to low expression level of the transgene, (3) if the extracellular region is too small, the immune system cannot respond and hence antibodies are difficult to produce, and (4) it is difficult to obtain antibodies against multi-transmembrane proteins among membrane proteins (Non-patent Document 2).

In another method reported, a functional membrane protein is reconstructed on the baculovirus membrane and used for immunization (Non-patent Document 3).

However, the above document shows that this method causes weak immune responses during induction of antibody specific to a target molecule. Moreover, such a method results in post-translational modifications (e.g., addition of complex N-linked sugar chains) different from those found in mammalian cells because baculovirus is prepared in insect cells, and there is a lot of uncertainty as to whether all membrane proteins can take their functional structure on the viral membrane.

To eliminate the need for considering the problems of three-dimensional structures, some methods are reported, which involve direct administration of grown cells to mouse tail vein or abdominal cavity to cause immune responses (Patent Documents 4 to 6 and Non-patent Documents 4 to 8). In these methods, 1 to $10 \times 10^6$ cells (corresponding to about 4 to 40 mg protein), which are larger than the normal antigen dose (100 to 200 μg target protein), are administered for a short period of time (at intervals of 1 week) and antibody-producing cells are collected from 1 to 6 weeks after the initiation of immunization.

For cell administration, an improved method is reported in which human cancer tissue is administered under the skin or into the gonadal fat pad in mice (Patent Document 7).

However, the methods disclosed in Patent Documents 4 to 6 and Non-patent Documents 4 to 8 require further studies for their practical use in the following points: (1) immune responses are difficult to occur against a specific substance because many kinds of proteins are immunized at the same time; (2) anaphylactic shock will be caused because proteins are administered in large amounts; and (3) animals are more likely to die earlier, e.g., due to organ failure caused by metastasis of cancer cells.

Moreover, to obtain many types of high-affinity antibodies, it is important to ensure the progress of hyperimmunization. In conventional methods, it is known that immunization with a lower antigen dose for a longer period of time is more likely to facilitate hyperimmunization. For example, multiple administrations (empirically 5 or more) at intervals of 3 weeks or longer are known to be preferred for mice (Non-patent Document 9). Hyperimmunization refers to a combination of the following three mechanisms: class shift to IgG; affinity maturation, and clonal dominance (apoptosis-induced selective death of antibody-producing cells with low specificity), and it is known as a mechanism which allows selective proliferation of high-affinity antibodies (Non-patent Document 9).

In the methods disclosed in Patent Documents 4 to 6 and Non-patent Documents 4 to 8, mice are more likely to die earlier and hyperimmunization is less likely to proceed, because a large amount of cells are administered for induction of immune responses. It is therefore difficult to sufficiently induce effective immune responses by the methods for direct cell administration disclosed in these documents.

Further, in the method disclosed in Patent Document 7, (1) it is necessary to isolate human tissues containing B cells, (2) immune responses are not reproducible due to differences in the types of cells contained in the tissues, and (3) in vitro culture is difficult and gene transfer or other techniques are also difficult to apply.

PRIOR ART DOCUMENTS

Patent Documents

Patent Document 1: JP 2001-010974 A
Patent Document 2: JP 07-188056 A
Patent Document 3: JP 07-313187 A
Patent Document 4: WO2006/109533
Patent Document 5: JP 06-327491 A
Patent Document 6: JP 2004-517885 A
Patent Document 7: JP 2001-520011 A Non-Patent Documents Non-patent Document 1: Folia Pharmacol. Jpn 2008 131 p. 102-108
Non-patent Document 2: Seibutsu Kogaku (Biotechnology) 2008 86(8) p. 384-386
Non-patent Document 3: J. Immunol. Methods 2007 322 (1-2) p. 104-117
Non-patent Document 4: Somatic Cell Genet. 1979 5(6) p. 957-971
Non-patent Document 5: J. Clin. Invest. 1981 68(5) p. 1331-1337
Non-patent Document 6: Cancer Res. 1986 46(10) p. 5137-5143
Non-patent Document 7: Cancer Res. 1982 42(2) p. 601-608
Non-patent Document 8: Proc. Natl. Acad. Sci. USA 1979 76(3) p. 1438-1442
Non-patent Document 9: Antibodies: A Laboratory Manual 1988 Chapter 5 p. 114-115

DISCLOSURE OF THE INVENTION

Problem to be Solved by the Invention

In view of the foregoing, there is a demand for the establishment of a simple method for preparing antibodies against membrane proteins.

Thus, the object of the present invention is to provide a method which is intended to overcome the problems stated above and which allows efficient preparation of a desired antibody.

Means to Solve the Problem

As a result of extensive and intensive efforts made to achieve the above object, the inventors of the present invention have found that a desired antibody can be obtained efficiently when cancer cells having a metastatic potential are transplanted into and engrafted in laboratory animals. This finding led to the completion of the present invention.

Namely, the present invention is as follows.

[1] A method for preparing an antibody-producing cell, which comprises the following steps:
(1) transplanting metastatic cancer cells capable of expressing a target antigen into a non-human animal to ensure engraftment of the cancer cells in the animal;
(2) immunizing the animal with the target antigen; and
(3) collecting the antibody-producing cell from the immunized animal.

[2] The method according to [1] above, which further comprises the step of immortalizing the collected antibody-producing cell.

[3] A method for preparing a hybridoma cell, which comprises the step of allowing the antibody-producing cell obtained by the method according to [1] above to be fused with a myeloma cell.

[4] A method for preparing an antibody or a fragment thereof, which comprises the step of isolating and expressing a gene encoding the antibody or fragment thereof from an immune tissue or organ of the immunized animal according to [1] above or from the antibody-producing cell or hybridoma cell obtained by the method according to any one of [1] to [3] above.

[5] A method for preparing an antibody against a target antigen, which comprises the step of collecting the antibody from the antibody-producing cell obtained by the method according to [2] above or from the hybridoma cell obtained by the method according to [3] above.

[6] A method for preparing an antibody, which comprises the following steps:
(1) transplanting metastatic cancer cells capable of expressing a target antigen into a non-human animal to ensure engraftment of the cancer cells in the animal;
(2) immunizing the animal with the target antigen; and
(3) collecting serum from the immunized animal.

[7] The method according to any one of [1] to [6] above, wherein the cancer cells are breast cancer cells.

[8] The method according to any one of [1] to [7] above, wherein the antigen is a membrane protein.

[9] The method according to any one of [1] to [8] above, wherein the site to be transplanted is a mammary gland.

Effects of the Invention

The present invention enables the provision of a novel immunization method by which a desired antibody can be obtained efficiently.

BRIEF DESCRIPTION OF THE DRAWINGS

FIG. 7A is an electrophoresis photograph confirming amplification of H chain and L chain, while FIG. 7B is a photograph showing the results of scFv protein purification. Lanes 1 and 2 represent before and after purification, respectively.

DESCRIPTION OF EMBODIMENTS

Figure 1:
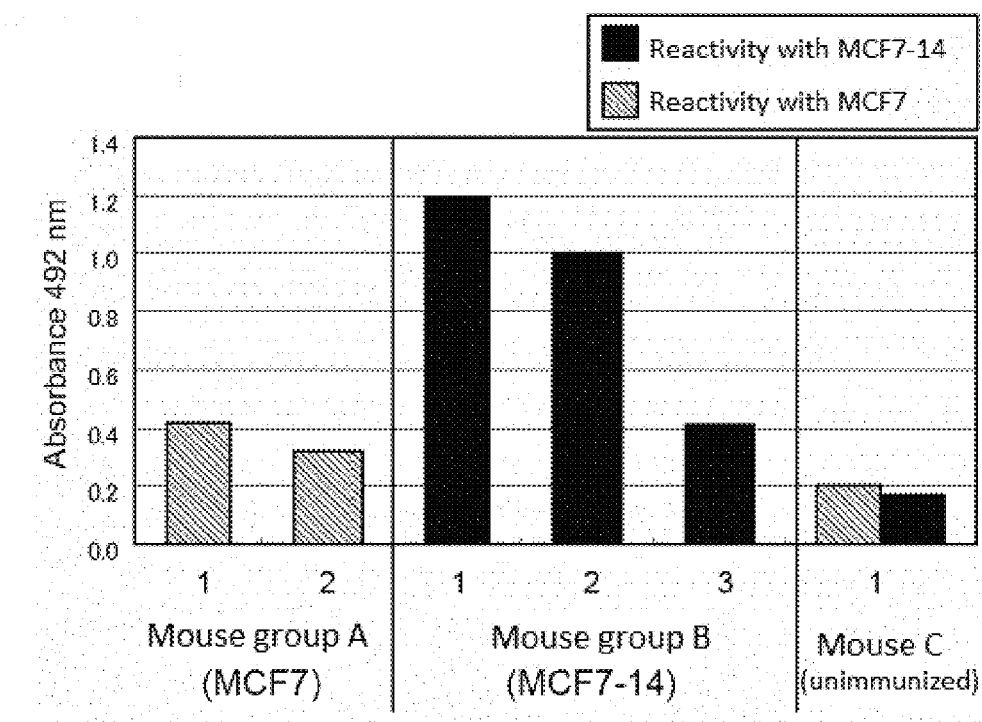
FIG. 1 shows the results analyzed for the titers of antibodies contained in plasma. Mouse group A is a group receiving MCF7 transplantation, mouse group B is a group receiving MCF7-14 transplantation, and mouse group C is an unimmunized group. The mouse groups A and B show reactivity with their transplanted cells, whereas the mouse group C shows reactivity with both MCF7 and MCF7-14.

The present invention will be described in more detail below with respect to preferred embodiments. It should be noted that the present invention is not limited to the following description of the embodiments and may be carried out with various modifications without departing from the spirit of the present invention.

The present invention is characterized in that animals are immunized with metastatic cancer cells capable of expressing a target antigen to be immunized, and is directed to methods for obtaining antibody-producing cells and antibodies from the animals thus immunized.

The method for antibody preparation according to the present invention comprises the following steps:

(1) transplanting metastatic cancer cells capable of expressing a target antigen into a non-human animal to ensure engraftment of the cancer cells in the animal;

(2) immunizing the animal with the target antigen; and (3) collecting antibody-producing cells from the immunized animal.

In the present invention, metastatic cancer cells capable of expressing a target antigen are transplanted into and engrafted in laboratory animals, whereby the animals can be immunized effectively to produce desired antibodies. According to the present invention, it is possible to obtain many types of antibody-producing cells in which hyperimmunization has proceeded sufficiently.

Any cells may be transplanted into laboratory animals as long as they are metastatic cancer cells capable of expressing a target antigen, and there is no particular limitation on animal species or organs from which the cancer cells are derived.

The method of the present invention comprises the step of immunizing an animal with a target antigen which is expressed by cancer cells having a metastatic potential. In standard techniques for antibody preparation, animals are immunized by being administered with an antigen in admixture with an adjuvant or the like. In contrast, the present invention is designed to immunize animals by transplantation of metastatic cancer cells into the animals, with the aim of increasing the immunization efficiency. In the present invention, these metastatic cancer cells are modified to express a target antigen, and their metastatic ability assists the antigen to travel into lymph nodes or blood vessels in vivo from the site where the cancer cells are transplanted and engrafted. As a result, efficient immunization would be possible.

Moreover, in the present invention, by allowing metastatic cancer cells to be directly used for immunization, antigens can be immunized while retaining their functional three-dimensional structure and post-translational modifications, so that antibodies against membrane proteins can be induced, which have been difficult to obtain. In the present invention, cancer cells are responsible for antigen expression, and antibodies can be obtained against antigens having their inherent three-dimensional structure (which means their structure found in an in vivo environment). For this reason, the present invention eliminates the need for any additional treatment, such as three-dimensional reconstruction of isolated proteins, and allows induction of antibodies having sufficient neutralizing capacity against antigens. Further, in the present invention, antibodies are induced not only against membrane proteins, but also against proteins in the cytoplasm and nuclei. Induction of immune responses against intracellular substances appears to be mediated by a mechanism in which macrophages or other cells decompose the transplanted cancer cells by their phagocytic action to present the intracellular substances as antigens.

As used herein, the term "metastatic" is intended to mean that metastasis is observed when assayed by a method used to evaluate the metastatic ability of cells. For example, in a case where cells are transplanted into laboratory animals, this term refers to a state that the cells form distant metastasis. Likewise, the term "metastatic cancer cells" refers to cancer cells having a metastatic potential. In some in vivo environments, cancer cells may not always metastasize although they have a metastatic potential, but such a possibility does not deny their "metastatic potential." Even when cancer cells do not actually metastasize, they can be used for immunization purposes.

As used herein, the phrase "having a high metastatic potential" is intended to mean that metastatic ability is observed at a high percentage when assayed by a method used to evaluate the metastatic ability of cells. For example, in a case where cancer cells are transplanted into laboratory animals, a state that the cancer cells form distant metastasis in at least 20% or more, preferably 40% or more, more preferably 60% or more of the laboratory animals receiving transplantation is expressed as "having a high metastatic potential."

As used herein, the term "distant metastasis" is intended to mean metastasis to an organ located away from the primary focus, but it also includes metastasis to an organ even adjacent to the primary focus as long as the organ is of different type from the primary focus.

As used herein, the target "antigen" to be immunized is intended to mean a substance capable of inducing immune responses, which is not limited in any way as long as it is expressed in cancer cells to be transplanted and causes antigen-antibody reaction. Examples of an antigen available for use include proteins, nucleic acids, peptides, sugars, and lipids, with proteins being preferred and membrane proteins being more preferred.

As used herein, the term "membrane protein" is intended to mean a protein adhered to a biomembrane. The membrane protein intended in the present invention includes integral membrane proteins which extend across the lipid bilayer or which are bound to the lipid bilayer via fatty acid chains or the like, as well as peripheral membrane proteins which are non-covalently bound to hydrophilic segments in the lipid bilayer or to other membrane proteins. In the present invention, membrane proteins may be of either multi-transmembrane type or single-transmembrane type.

As used herein, the phrase "expressing an antigen" is intended to mean that metastatic cancer cells contain an antigen in an amount sufficient to induce immune responses. If the antigen is a protein, this phrase not only means that metastatic cancer cells are modified to express a target antigen protein to be immunized by introduction of a gene encoding this protein, but it also means that metastatic cancer cells express their inherent proteins (e.g., membrane proteins of the cancer cells). Thus, the protein may be either a native protein expressed in cancer cells or a recombinant protein expressed by introduction of any gene into cells. Introduction of any gene into cells may be accomplished by using known genetic engineering procedures with a vector such as a plasmid. In this case, sugar chains added to the protein may also serve as antigens. It is possible to use either a single or several antigens. In either case, protein molecules are localized at any site in cells, for example, in the nuclei, in the cytoplasm, on the cell membrane, etc.

Likewise, the size of antigen is not limited in any way. When a protein is expressed as an antigen in cancer cells of the same animal origin and used for transplantation, it is preferred because the protein can stimulate immune responses while retaining its inherent three-dimensional structure and modifications (e.g., with sugar chains).

Examples of metastatic cancer cells include those derived from bone, lung, lymph node, skin, liver, pleura, brain, breast, mammary gland, urinary bladder, large bowel or colon. In the present invention, metastatic cancer cells may be established cell lines or may be cancer cells collected from animals having metastatic cancer cells. Moreover, the origin of metastatic cancer cells is not limited in any way as long as it is a living body from which cells can be collected, and preferred examples include mice, rats, guinea pigs, rabbits, dogs, cats, goats, sheep, horses, cows, pigs, monkeys, chimpanzees, chickens, humans and so on, with humans being more preferred.

Preferred metastatic cancer cells are breast cancer cells having a metastatic potential, as exemplified by MCF7.

More preferred metastatic cancer cells are breast cancer cells having a high metastatic potential. Specific examples of breast cancer cells having a high metastatic potential include MCF7-14 derived from MCF7, which was established from human breast cancer (WO2008/093886, Accession No. FERM BP-10944), MDA-MB231, MDA-MB361 and MDA-MB435. In addition to these breast cancer cells, other cancer cells having a high metastatic potential include HT-1080 (fibrosarcoma), HepG2 (liver cancer), T-24 (urinary bladder cancer), SW620 (large bowel cancer), A549 (lung cancer), SW480 (colon cancer) and A375 (melanoma).

In a case where the transplantation site of metastatic cancer cells is the proximity of mammary glands, preferred are breast cancer cells expressing one or more proteins selected from estrogen receptor, progesterone receptor and Her-2. Breast cancer cells expressing these proteins are more likely to proliferate in mammary glands and hence are effective in engraftment after transplantation.

As metastatic cancer cells, it is possible to use not only cells inherently having a metastatic potential, but also cancer cells prepared to acquire a metastatic potential through any means selected as appropriate by those skilled in the art, including introduction of a gene, administration of growth factor (e.g., hormone or cytokine), induction of a genetic mutation by UV irradiation or drug treatment, or isolation of cells carrying a spontaneous mutation or an acquired change in chromatin modifications.

As metastatic cancer cells, it is possible to use a single type of cancer cells or several types of cancer cells. However, a single type of cancer cells are preferred for use, and established cancer cell lines are particularly preferred for use.

Any non-human animals may be transplanted with cancer cells having a metastatic potential as long as the transplanted cells are engrafted in the animals to cause humoral immune responses in the animals. Hereinafter, non-human animals to be transplanted with cancer cells are referred to as "laboratory animals."

Such laboratory animals may be of any type, including mice, rats, guinea pigs, rabbits, dogs, cats, goats, sheep, horses, cows, pigs, monkeys, chimpanzees, chickens and so on. Preferred are rodents such as mice, rats and guinea pigs, and more preferred are mice. Further, these rodents are preferably immunodeficient animals, more preferably immunodeficient mice.

As laboratory animals, inbred or closed colony immunodeficient mice can be used. Specific examples of immunodeficient mice include BALB/c, C57BL/6 and ICR immunodeficient mice. Among them, female BALB/c-nu/nu mice are preferred because their reduced T cell functions facilitate engraftment of the transplanted cells and also because they are easy to keep. As laboratory animals, genetically modified animals can also be used, including human antibody-producing mice.

As used herein, the term "transplanting," "transplanted" or "transplantation" is intended to mean that cancer cells are transferred to and implanted in laboratory animals, and it excludes direct administration of cancer cells into the blood or abdominal cavity.

In the step of transplanting metastatic cancer cells into a laboratory animal, the cancer cells can be transplanted into the laboratory animal in a conventionally known manner.

For transplantation, metastatic cancer cells may be injected into laboratory animals not only in the form of a cell suspension, but also in the form of cells cultured into a two- or three-dimensional structure, such as a sheet form or a multi-layered structure.

Although there is no particular limitation on the number of metastatic cancer cells to be used for transplantation, it is preferably at least $0.1 \times 10^6$ cells, and it is desirable to use as much cells as possible within the range sufficient to effectively induce immune responses.

As to the number of cells used in conventional immunization methods via the tail vein or intraperitoneal route, $1 \times 10^6$ cells to $1 \times 10^7$ cells are required for the primary immunization and each booster. In the present invention, at least $0.1 \times 10^6$ cells may be used only for transplantation, and hence immune responses can be induced by a smaller number of cells than in the conventional methods.

For improved engraftment of metastatic cancer cells, it is desirable to inject a cell suspension in admixture with a scaffold material.

Any scaffold material may be used for this purpose as long as it serves as a scaffold for the growth of cancer cells to be engrafted. Preferred examples include gels, hydrogels and resins, which are composed of laminin, entactin, collagen, fibrin, agarose, polyvinyl alcohol, polyethylene glycol, polylactic acid, polyglycolic acid and so on as components.

As a scaffold material, a gel comprising laminin/entactin and collagen as its major components is preferred in terms of the hardness of the formed gel and/or good proliferation of the transplanted cells, with Matrigel (Becton Dickinson) being more preferred. Preferred examples of Matrigel include growth factor reduced Matrigel as disclosed in J. Steroid. Biochem. Molec. Biol. 1993 44(4-6) p. 671-673.

With respect to the transplantation site of metastatic cancer cells, any site may be used for this purpose as long as it is an organ or tissue in which the transplanted cells are easily engrafted.

Examples of an organ into which cancer cells having a metastatic potential are transplanted include an organ to which the primary focus of cancer from which such cancer cells are isolated belongs, and organs to which metastatic lesions belong. In the present invention, transplantation into an organ to which the primary focus belongs is referred to as orthotopic transplantation, while transplantation into organs to which metastatic lesions belong is referred to as heterotopic transplantation.

Organs to which metastatic lesions belong are intended to include actual organs for which the formation of metastatic lesions from the cancer cells have been reported, as well as possible organs for which distant metastasis will be presumed in cancer of the same type from statistical data.

In a case such as where breast cancer cells are used as metastatic cancer cells, orthotopic transplantation into the breast is possible, but it is also possible to use heterotopic transplantation into other organs in which metastasis occurs frequently, as exemplified by bone, lung, lymph node, skin, liver, pleura and brain. The organ receiving transplantation is preferably intended for orthotopic transplantation, and in the case of breast cancer cells, it is the breast, by way of example.

In the present invention, even if the animal species from which cancer cells are isolated is different from the animal species into which the cancer cells are transplanted, transplantation into an organ having the same functions falls within orthotopic transplantation.

As a tissue into which metastatic cancer cells are transplanted, preferred is the same tissue as that where the primary focus was formed. Other preferred examples are tissues in the proximity of lymph nodes, fat tissue, or tissues covered with fat tissue.

The tissue into which metastatic cancer cells are transplanted may be a tissue within the organ to which the primary focus belongs or within the organs to which metastatic lesions belong, as in the case of the same tissue as that where the primary focus was formed, or alternatively, may be a tissue outside the organ to which the primary focus belongs or outside the organs to which metastatic lesions belong, as long as metastatic cancer cells are engrafted in such a tissue.

As used herein, the phrase "the proximity of lymph nodes" is intended to mean the periphery of lymph nodes, preferably adjacent to lymph nodes.

Although the proximity of lymph nodes is not limited in any way, in the case of mice, it may be within 1 cm, preferably within 5 mm, and more preferably within 1 mm from the lymph node, by way of example. In the proximity of lymph nodes, the engrafted cells will be easily supplied to the lymph nodes, which facilitate stimulation of immune responses. Thus, the proximity of lymph nodes is preferred.

As used herein, the term "fat tissue" is intended to mean a tissue composed of fat cells and a tissue covered with fat tissue. Examples of a tissue covered with fat tissue include mammary glands.

Fat tissue is suitable as a transplantation site of cancer cells because this tissue is easy to surgically manipulate for transplantation and allows easy engraftment of cells. In a case where mice are used as laboratory animals for transplantation of breast cancer cells, the cells are preferably transplanted into mammary glands, for example, the fourth mammary gland. The fourth mammary gland is not only located in the proximity of lymph nodes and covered with fat tissue, but is also particularly easy to manipulate for transplantation among mammary glands and allows long-term engraftment.

Moreover, in the present invention, the transplantation site of metastatic cancer cells is not limited to the organ to which the primary focus of cancer cells belongs or the organs to which metastatic lesions belong, and any site may be possible as long as it allows engraftment of the transplanted metastatic cancer cells.

As used herein, the term "engrafted" or "engraftment" is intended to mean that the transplanted cancer cells stay at the site and proliferate to form cell aggregates.

For engraftment of metastatic cancer cells within laboratory animals, it is sufficient to keep these laboratory animals after transplantation of the cancer cells. Moreover, the immunization step in the present invention may be accomplished simply by keeping these laboratory animals for a period of time during which immune responses occur, and boosters, which are used in standard immunization, are not required for this purpose.

The reason why the present invention does not include any booster step would be because since the transplanted cancer cells have a metastatic potential, cancer cells having a metastatic potential may be constantly supplied from the engrafted site to lymph nodes or blood vessels to thereby continuously stimulate immune responses.

To obtain monoclonal antibodies with high affinity or specificity to antigens, it is important to ensure the progress of hyperimmunization. Thus, the period for keeping laboratory animals in the step of immunization is preferably as longer as possible within the range where the animals can survive.

The indicators of hyperimmunization include the size of spleen and the number of spleen cells. Since the size of spleen and the number of spleen cells reflect the degree of proliferation of antibody-producing cells, the variety of antibody-producing cells will increase with increase in the number of spleen cells. Namely, a larger number of spleen cells would allow production of antibodies with more improved performance.

If the laboratory animals are mice, the number of cells obtained from a non-sensitized mouse spleen is 0.5 to $1 \times 10^8$ cells. Upon immunization using an adjuvant or the like, it is known that the number of cells is increased up to 2 to $4 \times 10^8$ cells by repeated administration for 15 weeks, and hyperimmunization proceeds in such immunized mice. It is shown that antibodies having a certain affinity and specificity to desired antigens are obtained when the number of spleen cells is $3 \times 10^8$ cells or more.

The present invention is advantageous in that a small amount of cells are sufficient to achieve immunization, which prevents early death of laboratory animals.

In conventional methods in which cells are administered to the abdominal cavity or tail vein for immunization, the administered cells are more likely to disappear earlier due to the phagocytic action of macrophages or the like. Moreover, when metastatic cancer cells are administered to mice via the tail vein, the mice will die within a short period of time (within 1 to 6 weeks after transplantation) as a result of sudden stimulation of immune responses. In some actual cases, all mice died within 7 weeks after administration (Toagosei annual report TREND 1999 vol. 2, p. 32).

In the present invention, many mice receiving transplantation have been confirmed to survive over a long period of at least 10 weeks or longer, usually 15 weeks or longer. Further, since the present invention allows continuous supply of cancer cells, immune responses are stimulated continuously, hyperimmunization proceeds efficiently, and the number of spleen cells can be increased to 9 to $13 \times 10^8$ cells.

In the present invention, hyperimmunization may proceed within a short period of time in some cases, depending on the type of antigen or cell to be transplanted, the number of cells to be transplanted, etc. In such cases, the keeping of the animals may be stopped earlier for collection of antibody-producing cells as described later.

A preferred antigen to be expressed by cancer cells having a metastatic potential is a protein, and examples of a desired protein include, but are not limited to, membrane proteins.

Antibodies to be prepared in the present invention are intended to mean polyclonal antibody, monoclonal antibody, recombinant antibody, an antibody fragment (i.e., a part of antibody), smaller antibody, multi-specific antibody, modified antibody, etc., and are not limited in any way as long as they have antigen-binding capacity. Examples include H chain, L chain, Fv, Fab, Fab', F(ab')2, scFv, sdFv, sc(Fv)2, dsFv, Diabody, chimeric antibody, humanized antibody, human antibody, single chain antibody, multi-specific antibody (e.g., bispecific antibody), labeled antibody and so on.

In the present invention, metastatic cancer cells are transplanted into and engrafted in laboratory animals to thereby achieve immunization of the animals. Following such an immunization step, antibody-producing cells can be obtained in the present invention, according to procedures well known to those skilled in the art.

In the present invention, after the laboratory animals are immunized with the metastatic cancer cells engrafted therein, sera may be collected from the laboratory animals to prepare polyclonal antibodies.

Alternatively, antibodies can also be collected from the antibody-producing cells obtained in the present invention. Antibody collection may be accomplished in any known manner, for example, by culturing antibody-producing cells and collecting antibodies from the cultured product.

Moreover, in the present invention, a gene encoding an antibody or a fragment thereof (hereinafter also referred to as an "antibody gene") may be cloned (isolated) from an immune tissue or organ of the immunized animal or from antibody-producing cells to thereby prepare the antibody or fragment thereof.

Such an antibody gene may be cloned from an immune tissue or organ, either directly or after preparing a fraction of antibody-producing cells from the immune tissue or organ.

Examples of an immune tissue or organ include spleen, lymph node, peripheral blood and the like. Such an immune tissue or organ may be either the whole or a part of an immune tissue or organ taken from one laboratory animal, or alternatively, may be prepared in a non-uniform state, e.g., by mixing immune tissues or organs taken from a plurality of laboratory animals.

Antibody-producing cells refer to cells (e.g., B cells) which are present in the body of laboratory animals and produce antibodies. Antibody-producing cells may be collected from immune tissues or organs such as spleen, lymph node, peripheral blood and the like, preferably from spleen or lymph node and more preferably from spleen. Antibody-producing cells are fractionated into one to several tens of types of cells, preferably one to several types of cells.

Cell fractionation may be accomplished in a known manner, for example, by extracting spleen cells from the spleen to prepare a cell suspension. Then, cells in the suspension may be separated using a cell sorter or magnetic beads, micropipets, limiting dilution, microwell arrays, etc.

Cloning of the antibody gene may be accomplished in any manner. Preferably, cDNA is synthesized from mRNA using reverse transcriptase, followed by PCR to amplify antibody VH and VL genes. Then, a gene encoding the desired antibody is constructed and integrated into a vector suitable for screening as described later.

For example, if scFv is to be obtained, VH and VL genes are ligated via linker DNA during gene construction. Alternatively, if chimeric antibody is to be obtained, a human constant region gene is ligated to each variable region gene. The resulting construct is ligated to an expression vector and this expression vector is introduced into a host (prokaryotic or eukaryotic organism) to express the construct, thereby preparing the desired antibody. With respect to Fab, Fab', F(ab')2, scFv, sdFv, sc(Fv)2, dsFv and Diabody, genes encoding the respective fragments may each be obtained and expressed by being ligated to an expression vector, as in the case described above.

For preparation of humanized antibody, complementarity determining regions (CDRs) are grafted from each mouse antibody variable region to each human variable region, along with using framework regions (FRs) of human origin. This procedure is called CDR grafting, and CDRs are used to prepare a reconstructed variable region of mouse origin. Then, these humanized reconstructed human variable regions are connected to human constant regions. Such procedures for humanized antibody preparation are well known in the art (Protein Eng. 1991 4(7) p. 773-83).

For preparation of multi-specific antibody, two or more types of antibodies differing in their functions (e.g., specificity) are joined together by gene recombination technology. Such procedures are well known in the art (Structure 1994 2(12) p. 1121-1123).

Likewise, for preparation of labeled antibody, a desired labeling compound is chemically attached via a covalent bond to a sulfhydryl group or an amino group in an antibody molecule by using maleimide or succinimide, etc. Procedures for antibody labeling are well known in the art (Immobilized Affinity Ligand Techniques Academic Press Chapter 3 p. 137-279).

Antibody screening may be accomplished in any manner. Preferably, antibodies are screened by being expressed in animal cells or by being presented on the surface of cells or structures through display techniques for protein molecules.

Antibody expression in animal cells may be accomplished in a known manner. For example, a vector carrying an antibody gene is introduced into cells suitable for protein expression (e.g., CHO cells, COS cells, 3T3 cells), followed by culturing the cells to secrete antibody molecules. The collected antibody molecules are screened by immunochemical assay (e.g., enzyme immunoassay) to thereby select an antibody with specificity and desired affinity to the antigen. Alternatively, a desired antibody can also be isolated by using flow cytometry, binding events between magnetic beads and a magnet, etc.

Antibody presentation on the surface of cells or structures may be accomplished in a known manner, as exemplified by phage display, yeast display, bacteria display, liposome display, etc. In the case of using phage display, for example, E. coli cells are transformed with a phagemid vector carrying an antibody gene and then further superinfected with a helper phage to thereby prepare a phage library expressing the antibody gene (i.e., presenting the antibody). Then, phages specific to the antigen are concentrated by biopanning to select a desired antibody. Alternatively, a desired antibody can also be selectively collected by using interaction between biotin and streptavidin, enzyme immunoassay, flow cytometry, etc.

After the antibody is selected, the antibody can be obtained by being separated from the structures (e.g., phages) or by infecting the structures into E. coli or other cells. Alternatively, a gene encoding the antibody can be used to convert into an antibody having a desired structure by gene recombination.

In the present invention, antibodies can also be prepared by immortalization of antibody-producing cells. Techniques for immortalization include commonly used techniques for fusing tumor cells (e.g., myeloma cells) with antibody-producing cells to thereby form hybridomas, as well as other techniques for infecting cells with a virus or for introducing a gene into cells. Examples of a virus available for this purpose include Epstein-Barr virus (EBV), human papilloma virus (HPV), SV40 and so on. Examples of a gene to be introduced include genes encoding telomerase, SV40 large T antigen, HPV E6 or E7, adenovirus E1A, hTERT, bmi-1, c-myc and so on. Any combination of these genes may also be used for this purpose.

For preparation of hybridomas, commonly available established cell lines of animal (e.g., mouse) origin may be used as myeloma cells to be fused with antibody-producing cells. Cell lines preferred for use are those having drug selectivity and having the property of being unable to survive in an unfused state in HAT selective medium (containing hypoxanthine, aminopterin, thymidine) and able to survive only in a state fused with antibody-producing cells.

Examples of myeloma cells include mouse myeloma cell lines such as P3-X63.Ag8(X63), P3-X63.Ag8.U1 (P3U), P3/NS 1/1-Ag4-1(NS1), Sp2/0-Ag14(Sp2/0), etc. In the selection of myeloma cells, compatibility with antibody-producing cells should be considered, as appropriate.

For cell fusion, antibody-producing cells at $1 \times 10^6$ to $1 \times 10^7$ cells/ml and myeloma cells at $2 \times 10^5$ to $2 \times 10^6$ cells/ml are mixed in a serum-free medium for animal cells (e.g., DMEM or RPMI-1640 medium). The ratio between antibody-producing cells and myeloma cells is 1:1 to 10:1, preferably 5:1. Then, fusion reaction is performed in the presence of a cell fusion promoter. As a cell fusion promoter, it is possible to use polyethylene glycol with an average molecular weight of 1000 to 6000 daltons (Da), etc. Alternatively, a commercially available cell fusion apparatus based on electrical stimulation (e.g., electroporation) may also be used to fuse antibody-producing cells with myeloma cells.

Viruses are available from biological resource banks such as ATCC (American Type Culture Collection). By way of example, EBV may be introduced according to the known transform method (D. Kozbor et al., Methods in Enzymology, 121 140 (1986)), etc.

Moreover, the above genes for use in immortalization may be obtained by gene amplification from cancer cells or the like, and may be introduced by electroporation, lipofection, DNA particle gun, calcium phosphate transfection, or other techniques.

In embodiments of the present invention where antibody-producing cells are immortalized, the cells are cultured to secrete antibody molecules, followed by the same screening as described above for antibody expression in animal cells to thereby select cells producing an antibody specific to the antigen.

Then, the antibody is collected from the selected cells. Techniques used for antibody collection are not limited in any way, and any known procedure may be used for this purpose. For example, the cells may be cultured to produce the antibody, or alternatively, a gene for the antibody may be cloned from the cells and subjected to, e.g., recombination to produce the antibody by bacteria, yeast cells, animal cells, viruses, etc. Culture may be performed in vitro or may be performed in mice or other animals by intraperitoneal administration of the cells to obtain the ascites. For cloning of the antibody gene, cDNA is synthesized from mRNA of each cell using reverse transcriptase, followed by PCR to amplify antibody VH and VL genes, as in the case described above. After amplification, a gene encoding the desired antibody is constructed and the antibody is obtained using a vector and cells suitable for antibody expression.

In the case of obtaining immunoglobulins as antibodies, they may be cleaved with enzymes to yield antibody fragments including Fv, Fab, Fab', F(ab')2, etc. More specifically, Fab is prepared with papain, while F(ab')2 is prepared with pepsin.

According to the above procedures, antibodies having various structures can be stably prepared against a target molecule.

According to the present invention, high immune responses can be induced, and hence the method for antibody preparation according to the present invention is very advantageous in the production of high-affinity antibodies recognizing membrane proteins.

EXAMPLES

The present invention will be further described in more detail by way of the following examples and comparative examples, which are not intended to limit the technical scope of the invention.

Example 1

Preparation of Antibodies Against Membrane Proteins (1) Cells

MCF7 and MDA-MB231 were purchased from the Institute of Development, Aging and Cancer, Tohoku University (TKG 0479) and the American Type Culture Collection (ATCC, Manassas, Va., USA), respectively.

MCF7-14 was obtained under Accession No. FERM BP-10944 and subcultured before use.

MCF7, MCF7-14 and MDA-MB231 were each cultured and subcultured at 37° C. under 5% $CO_2$ for 48 to 72 hours in RPMI1640 medium (Sigma) containing 10% (v/v) serum (EQUITECH-BIO), such that cell confluency did not exceed 80%.

(2) Transplantation of Cells

The proliferated cells were collected and washed twice with PBS(−) (0.01 M sodium-phosphate buffer, 0.138 M NaCl, 0.0027 M KCl, pH 7.4). The washed cells were suspended at a final density of $8.6 \times 10^7$ cells/mL in growth factor reduced Matrigel (Becton Dickinson) and stored on ice before use in transplantation.

Chloral hydrate (Sigma) was dissolved at a concentration of 3.5% (w/v) in physiological saline to prepare a 3.5% solution of chloral hydrate in physiological saline. Nude mice at 6 to 8 weeks of age (BALB/cALcl-nu/nu line (CLEA Japan, Inc., Japan)) were anesthetized by being intraperitoneally administered with 0.2 mL of the 3.5% solution of chloral hydrate in physiological saline. Into the fourth mammary glands in each mouse, the cells suspended in the Matrigel were transplanted at $1 \times 10^6$ cells per mammary gland via a 24 G injection needle, such that the cells did not extend off the mammary gland. Each mouse received two transplantations, one at left and another at right fourth mammary gland in the trunk.

In this method, no booster was used, unlike standard immunization.

(3) Collection of Plasma Fractions

After transplantation, the mice were kept for 15 weeks or longer. Cancer formation at each transplantation site was visually and palpably monitored over time. From the cancer cell-transplanted mice and the unimmunized mice, 20 μl, of blood was collected via the tail vein. Each collected blood was mixed with 1 μL heparin solution (Ajinomoto Pharma Co., Ltd., Japan). The resulting mixture was centrifuged at 3000×g for 5 minutes to precipitate the cells. The supernatant was collected as a plasma solution.

(4) Analysis of Immune Responses

MCF7, MCF7-14 and MDA-MB231 cultured in (1) above were each seeded at 80% confluence in a 96-well plate and cultured at 37° C. under 5% $CO_2$ for 16 hours.

After removal of the culture supernatant, 100 μL of a 10% (v/v) neutral buffered formalin solution (WAKO) was added and reacted for 10 minutes at room temperature. After removal of the formalin solution, each plate was washed three times with PBS(−) and then air-dried to give a plate in which the cells of each type were immobilized.

The plasma solutions collected in (3) above were each diluted 20,000-fold with TBS-T (25 mM Tris, 150 mM NaCl, 0.05% (v/v) Tween-20, pH 7.4). As a primary antibody, each plasma dilution was added in a volume of 100 µL per well in the immobilized plates and reacted at room temperature for 1 hour. Each well was washed three times with 200 µL TBS-T.

As a secondary antibody, anti-mouse IgG polyclonal antibody-HRP label (BETHYL) was diluted 5,000-fold with TBS-T. This antibody dilution was added in a volume of 100 µL per well and reacted at room temperature for 30 minutes. Each well was washed three times with 200 µL TBS-T.

Orthophenylenediamine (Sigma) was diluted with 50 mM carbonate-citrate buffer (pH 5.0) to give a final concentration of 0.5 mg/mL, and mixed with 1/10,000 volumes of 35% (w/w) aqueous hydrogen peroxide (WAKO). This mixture was added as a substrate solution in a volume of 100 µL per well and reacted at room temperature for 10 minutes. 25 µL of 3 N sulfuric acid (WAKO) was added to stop the reaction. The absorbance at 492 nm was measured with a plate reader (SpectraMaxPure384, Molecular Devices) to analyze the titer in each plasma solution.

FIG. 1 shows the results analyzed for the titers of antibodies contained in plasma of the MCF7- or MCF7-14-transplanted mice and unimmunized mice.

In comparison with the unimmunized mice, the mice transplanted with MCF7 having a metastatic potential showed antibody production at higher levels, and the mice transplanted with more metastatic MCF7-14 clearly showed antibody production. In the mice transplanted with MDA-MB231 also showed antibody production (data not shown).

(5) Spleen Size and the Number of Leukocytes Contained in Spleen

The spleen is an organ responsible for proliferation and differentiation of B cells. When a foreign material enters the body and stimulates humoral immune responses, this organ plays a role in specifically increasing the number of B cells which produce antibodies recognizing the foreign material. Based on this fact, the number of leukocytes contained in the spleen can be used as one of the indicators for immune responses against an antigen.

From the mice transplanted with the cells in (2) above, spleen tissues were excised and compared for their size.

Figure 2:
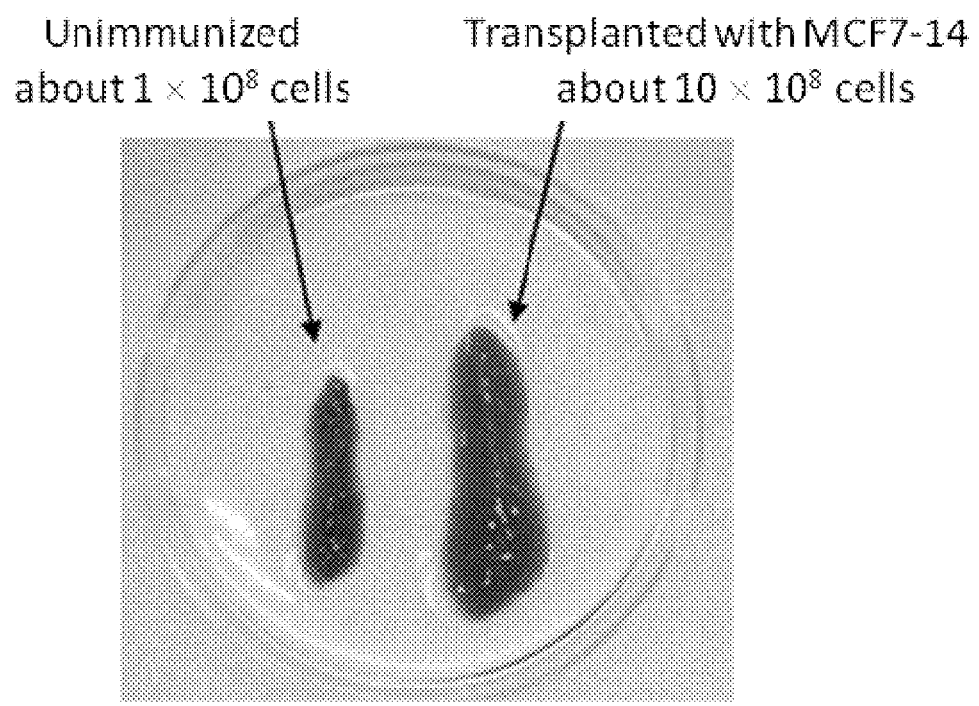
FIG. 2 shows a photograph of excised spleens on a culture dish of 6 cm diameter. This photograph shows spleens from the unimmunized group and the group receiving MCF7-14 transplantation.

In comparison with the unimmunized spleens, the spleens of the MCF7-14-transplanted mice were clearly enlarged (FIG. 2). The MDA-MB231-transplanted mice showed similar spleen enlargement, as in the case of MCF7-14 (data not shown).

Figure 3:
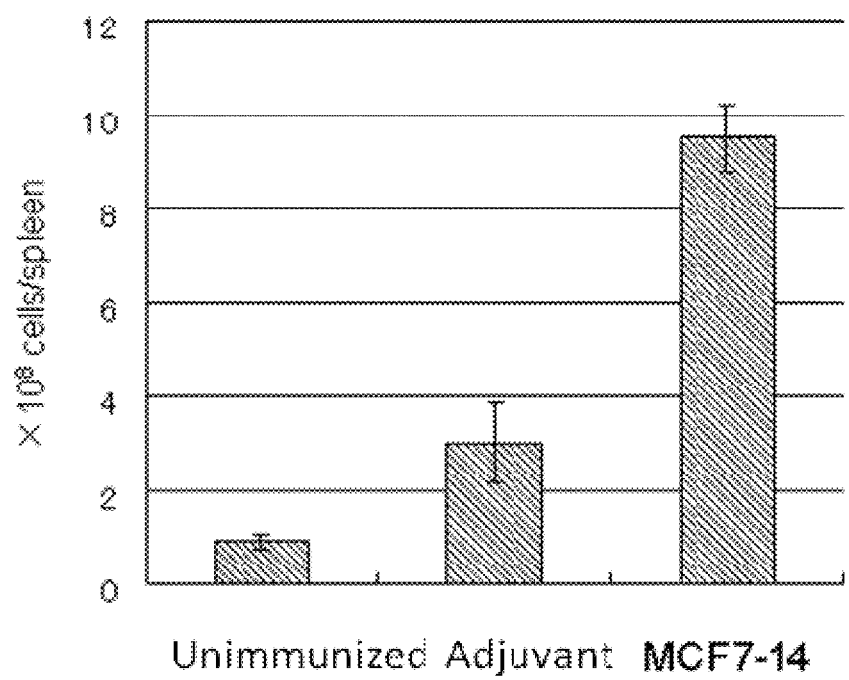
FIG. 3 shows the results calculated for the number of spleen cells, in which each error bar represents standard deviation.

To calculate cell counts in each case, cells in each spleen were collected into RPMI1640 medium using an injection needle and a pair of tweezers to give a cell suspension. The cell suspension (100 µL) and Turk's solution (900 µL, Nacalai Tesque, Inc., Japan) were mixed together. The leukocyte concentration was measured with a hemacytometer (AS ONE Corporation, Japan) and used to calculate the number of leukocytes per spleen. As a result, the unimmunized mice had 0.8 to $1 \times 10^8$ leukocytes per spleen, whereas the MCF7-14-transplanted mice had $10 \times 10^8$ leukocytes, which increased about 10-fold. FIG. 3 shows the number of spleen cells (the number of leukocytes per spleen) obtained from two unimmunized mice, 100 mice receiving standard immunization using adjuvants (e.g., Freund's complete adjuvant (PIERCE), incomplete adjuvant (PIERCE), Ribi adjuvant system (Funakoshi Co., Ltd., Japan), GERBU adjuvant (Nacalai Tesque, Inc., Japan)), and three mice transplanted with MCF7-14. In comparison with the immunization using adjuvants which resulted in up to 2 to $4 \times 10^8$ cells, the method of the present invention was confirmed to induce high immune responses never before achieved.

(6) Cell Fusion

MCF7-14-transplated mouse spleen lymphocytes were fused in a standard manner with mouse myeloma cell line P3X63-Ag8 (ATCC Accession No. CRL-1580) using 50% (v/w) polyethylene glycol 4000 (Sigma).

The fused cells were suspended in HAT medium (Invitrogen) and dispensed into twenty 96-well plates in a volume of 100 µL per well. During culture, 200 µL of HAT medium was added to each well. After culture for 11 to 16 days, the plates were observed under a microscope, indicating that 3 to 6 colonies were formed per well.

(7) Analysis of Hybridoma Cells

From the 96-well plates showing the growth of hybridoma cells, the culture supernatants were collected in 200 µl volumes and analyzed for reactivity with cells in the same manner as shown in (4) above to screen antibodies capable of reacting with MCF7-14.

Among the antibody-producing hybridoma cells thus obtained, five hybridoma cells were randomly selected and monocloned. These cells were cultured in HT medium (Invitrogen), followed by immunostaining against MCF7-14 using antibodies contained in the supernatants and FITC-labeled anti-mouse IgG (Becton Dickinson).

Figure 4:
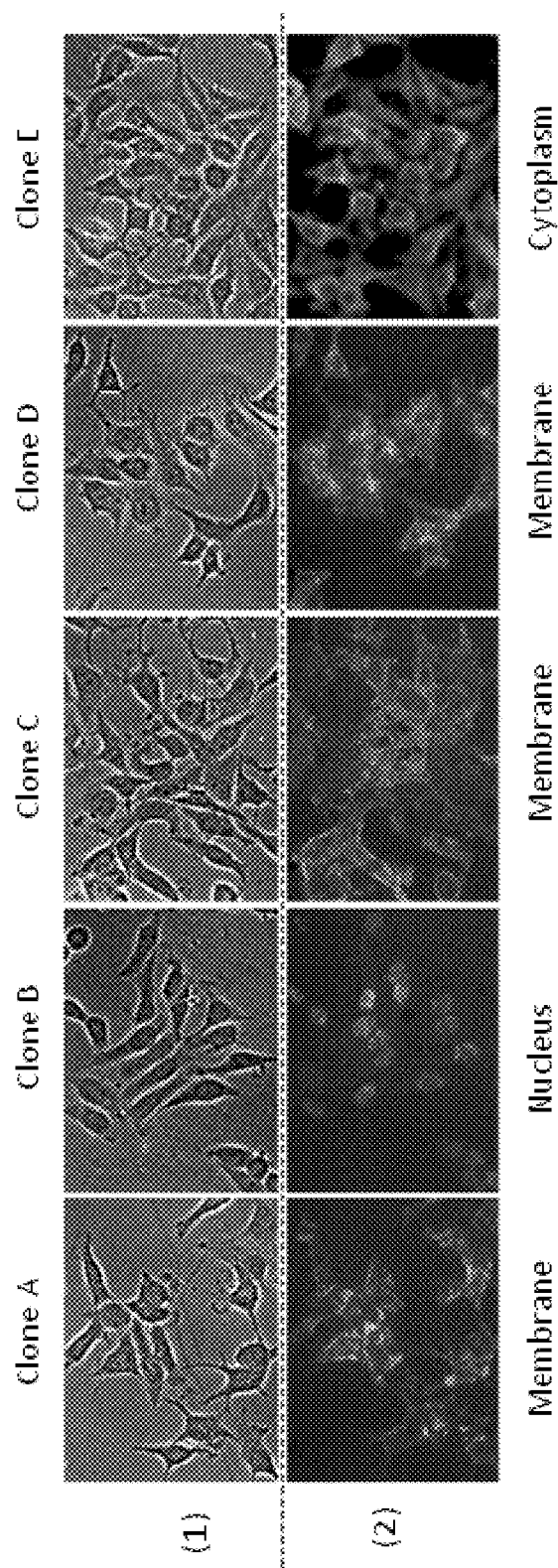
FIG. 4 shows images of immunostaining observed under a phase contrast microscope (1) and under a fluorescent microscope (2).

FIG. 4 shows the results observed for cell morphology under a phase contrast microscope (1) and the results detected for the stained regions under a fluorescent microscope (2).

Among the antibodies obtained from the five types of hybridoma cells, three antibodies (clones A, C and D) were found to recognize cell membrane proteins, while the remaining antibodies were found to recognize proteins present in the nuclei (clone B) and the cytoplasm (clone E), respectively. The result showing that three (60%) of the five clones randomly selected were antibodies against membrane proteins strongly indicates that the immunization method of the present invention is a procedure allowing easy preparation of antibodies against membrane proteins, which have been difficult to prepare.

Example 2

Preparation of Antibodies Against Membrane Protein (F3)

(1) Antigen

Human tissue factor (coagulation factor III, F3), which is a membrane-bound protein, is a factor responsible for the initiation of extrinsic blood coagulation reaction. Antibodies against this membrane protein were prepared.

(2) Construction of Expression Vector

RNA extracted from HeLa cells using an SV Total RNA Isolation System (Promega) was converted into cDNA using SuperScriptIII RNase H-Reverse Transcriptase (Invitrogen), and this cDNA was used as a template in PCR to amplify F3. The amplified fragment was cloned into pEF6/Myc-H isA (Invitrogen) such that the Tag sequence was deleted. Each manipulation was conducted in accordance with the document attached to the kit.

(3) Gene Expression on Cells

Into MDA-MB231 described in Example 1(1), the plasmid constructed in (2) above was introduced using FUGENE6 (Roche Applied Science). The manipulation was conducted in accordance with the document attached to the kit. The cells were cultured in the same medium as shown in Example 1(1)

supplemented with 10 µg/mL blasticidin S hydrochloride while repeating medium replacement every 3 to 5 days to select drug-resistant cells. To pick out cells showing forced expression of F3 from among the resulting resistant strains, the expression level of F3 was confirmed in the same manner as shown in Example 1(4) by cell-based enzyme immunoassay (ELISA). It should be noted that Anti Coagulation Factor 3/Tissue Factor (R&D systems), which is anti-F3 polyclonal antibody, was diluted to 1 µg/mL for use as a primary antibody. Peroxidase AffmiPure Goat anti-bovine IgG (H+L) (Jackson ImmunoResearch) was used as a secondary antibody. In addition, TMB+(DAKO) was used as a substrate solution and the absorbance at 450 nm was measured with a plate reader to analyze antibody titers.

Figure 5:
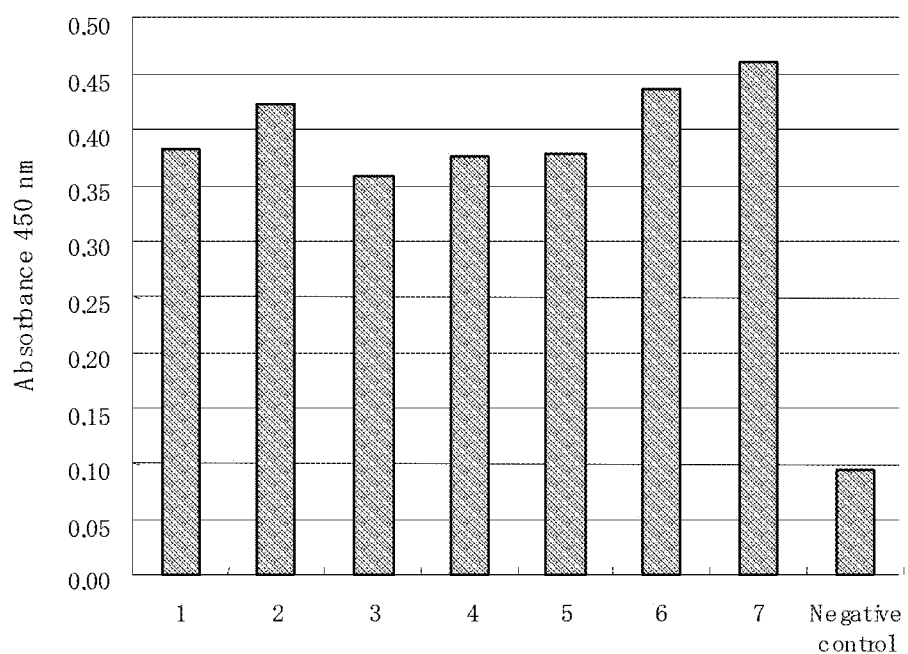
FIG. 5 shows the results confirmed for antigen protein expression in cells. The vertical axis represents the reactivity between F3 gene-transformed cells (1 to 7) or non-transformed cells (Negative control) and F3-recognizing antibody.

FIG. 5 shows the results of expression analysis with anti-F3 polyclonal antibody performed on the F3 gene-transformed cells (1 to 7) and non-transformed cells (Negative control).

The transformed cells were found to show significantly increased F3 expression when compared to the non-transformed cells.

(4) Transplantation of F3-Expressing Cells

Among these cells confirmed to express F3, five types of cells (1 to 5) showing substantially uniform growth were selected and cultured. The grown cells were collected with trypsin and washed twice with PBS(−). These five types of cells were mixed to a uniform state and then transplanted into mice in the same manner as shown in Example 1(2). In this method, no booster was used, unlike standard immunization.

(5) Obtaining of Monoclonal Antibodies

At 7 months after transplantation, spleen cells were collected and used to prepare hybridoma cells in the same manner as shown in Example 1(6). To select hybridoma cells producing antibodies recognizing F3, ELISA using F3 protein was performed as follows to analyze the titers of antibodies produced by the hybridoma cells.

A recombinant F3 protein (Coagulation Factor III/Tissue Factor, human, Recombinant, Carrier-free, R&D systems) was diluted to 2 µg/mL in PBS(−) and dispensed in 100 µL volumes into 96-well plates. After adsorption for 1 hour at room temperature, the plates were blocked for 30 minutes at room temperature with a solution prepared to contain 1% (w/v) bovine serum albumin in PBS(−). After the 96-well plates were washed with TBS-T, the same procedure as shown in Example 1(4) was repeated, except that antibody contained in each culture supernatant of hybridoma cells was used as a primary antibody and a solution of anti-mouse IgG polyclonal antibody-HRP label (BETHYL) diluted 5,000-fold in TBS-T was used as a secondary antibody.

Figure 6:
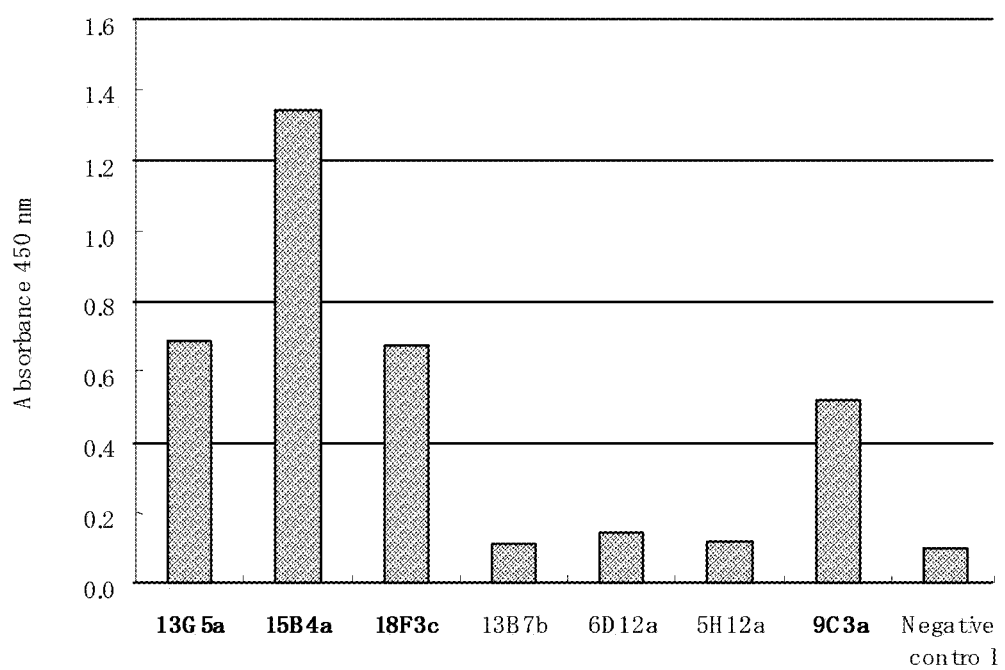
FIG. 6 shows the results analyzed for the titers of antibodies contained in hybridoma culture supernatants, in comparison with medium alone (Negative control). The vertical axis represents the reactivity of each antibody to F3 protein.

FIG. 6 shows the results analyzed for the titers of antibodies produced by the hybridoma cells (indicated with their clone number), in comparison with medium alone (Negative control).

Against the membrane protein F3 expressed by cells, several monoclonal antibodies were obtained, as typified by clones 13G5a, 15B4a, 18F3c, 9C3a, etc.

Example 3

Gene Cloning from Hybridoma Cells and Preparation of scFv (1) Cloning of Antibody Gene and Construction of scFv Gene Monoclonal antibody recognizing antigen X was prepared in the same manner as shown in Example 2. From the resulting hybridoma cells, total RNA was extracted using an RNeasy Mini Kit (QIAGEN) according to the recommended protocols. The extracted total RNA was reverse transcribed using a SuperScript III One-Step RT-PCR system with Platinum Taq High Fidelity (Invitrogen) to obtain cDNA. The resulting cDNA was used as a template to amplify H and L chains with the following primers.

```
Primers for H chain
                                        (SEQ ID NO: 1)
Forward: TGAGGAGACGGTGACCGTGGTCCCTTGGCCCCAG (SEQ ID NO: 2)
Reverse: AGGTSMARCTGCAGSAGTCWGG
(R: A or G, M: A or C, S: C or G, W: A or T)

Primers for L chain
                                        (SEQ ID NO: 3)
Forward: GTTAGATCTCCAGCTTGGTCCC (SEQ ID NO: 4)
Reverse: GACATTCAGCTGACCCAGTCTCCA
```

PCR reaction was performed by pre-incubating at 94° C. for 10 minutes and repeating the following cycle 24 times: denaturation at 94° C. for 30 seconds, followed by annealing/elongation at 72° C. for 1 minute, to thereby amplify gene fragments.

Figure 7:
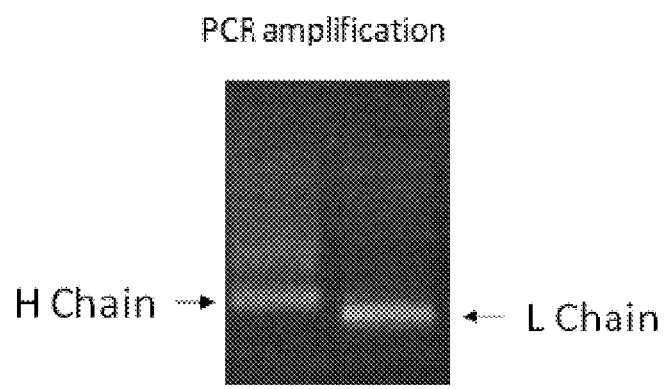
Figure 7:
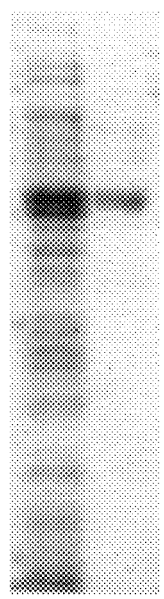

FIG. 7A shows the results of PCR amplification. A restriction enzyme site was added to each amplified fragment using primers for restriction enzyme addition, and the H and L chains were liked to each other via a linker. The sequences used for these primers are as shown below.

```
H chain
                                        (SEQ ID NO: 5)
Forward: GCGGCCATGGCCGTGCAACTGCAGCAGTCAGG (SEQ ID NO: 6)
Reverse: GTCGTCGACCGATCCGCCACCGCCAGAGCCACCTCCGCCTG
AACCGCCTCCACCTGAGGAGACGGTGACCGTGG L chain
                                        (SEQ ID NO: 7)
Forward: CGGTCGACGACATTCAGCTGACCCAGTC (SEQ ID NO: 8)
Reverse: CCGCTCGAGCGATCTCCAGCTTGGTCCCAG
```

The reverse primer for H chain is designed to contain a linker sequence (amino acid sequence: SSGGGGSGGGGSGGGGS (SEQ ID NO: 9)) for linking the H and L chains, as well as a Tag sequence (amino acid sequence: HHHHHH (SEQ ID NO: 10)) for purification purposes.

(2) Expression and Purification of scFv

The gene constructed as described in (1) above was cloned into pET32b (Noavagen) and the resulting recombinant plasmid was used to transform E. coli cells (BL21(DE3)) for protein expression. The cells were cultured in LB medium (10 g/L tryptone, 5 g/L yeast extract, 10 g/L sodium chloride, 100 µg/L ampicillin, 1% (w/v) glucose), and at the time point where the turbidity at 600 nm reached 0.4, IPTG was added at a final concentration of 0.4 mM, followed by culturing for 3 hours. The cells were collected and homogenized with CellLytic1B (SIGMA), and the centrifuged supernatant was purified with Ni Sepharose 6 Fast Flow (QIAGEN).

FIG. 7B shows the SDS-PAGE electrophoresis pattern of scFv protein before and after purification.

(3) Activity assay

A 96-well plate was coated at 50 ng/well with antigen X in PBS and allowed to stand at room temperature for 1 hour. After removal of the antigen solution, skimmed milk was dissolved at 5% (w/v) in TBS-T (25 mM Tris, 150 mM NaCl, 0.05% (v/v) Tween-20, pH 7.4) and added to each well in a volume of 300 µL, followed by blocking for 30 minutes. After washing with TBS-T, scFv diluted to 2000, 200 or 20 ng/ml was added as a primary antibody in a volume of 100 μl, per well and reacted at room temperature for 1 hour. Each well was washed three times with 200 μL TBS-T. As a secondary antibody, anti-mouse IgG polyclonal antibody-HRP label (BETHYL) was diluted 10,000-fold with TBS-T, added in a volume of 100 μL per well and reacted at room temperature for 30 minutes. After washing each well, orthophenylenediamine (Sigma) was diluted with 50 mM carbonate-citrate buffer (pH 5.0) to give a final concentration of 0.5 mg/mL, and mixed with 1/10,000 volumes of 35% (w/w) aqueous hydrogen peroxide (WAKO). This mixture was added as a substrate solution in a volume of 100 μL per well and reacted at room temperature for 10 minutes. 25 μL of 3N sulfuric acid (WAKO) was added to stop the reaction, and the absorption at 492 nm was measured with a plate reader (SpectraMax-Pure384, Molecular Devices) to analyze the titer of scFv.

Figure 8:
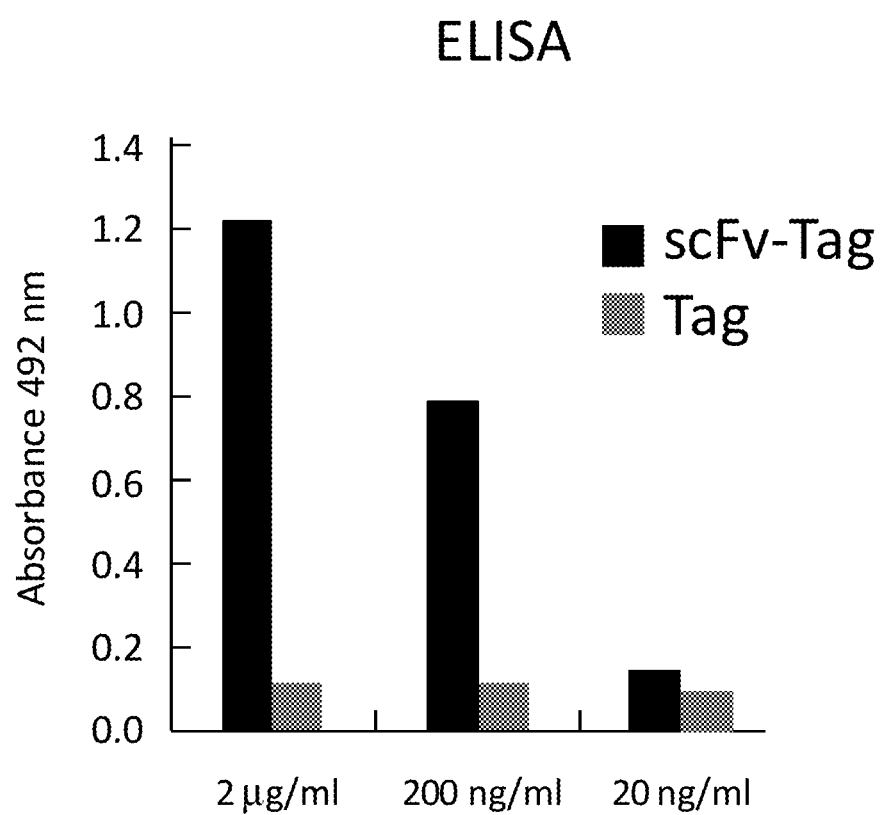
FIG. 8 shows the results measured for scFv activity by ELISA.

FIG. 8 shows the results measured for scFv activity. In comparison with the Tag sequence for purification purposes, scFv was found to have sufficient antigen-binding activity.

INDUSTRIAL APPLICABILITY

The present invention enables the preparation of antibodies which have been difficult to obtain by conventional methods.

Moreover, the present invention also enables the preparation of antibodies against the inherent three-dimensional structure of antigens, and hence enables the provision of antibodies having sufficient neutralizing capacity against the antigens.

The present invention makes it possible to provide a new material on the market as a novel antibody for clinical laboratory tests or therapeutic purposes.

SEQUENCE LISTING FREE TEXT

SEQ ID NO: 1: Synthetic DNA
SEQ ID NO: 2: Synthetic DNA
SEQ ID NO: 3: Synthetic DNA
SEQ ID NO: 4: Synthetic DNA
SEQ ID NO: 5: Synthetic DNA
SEQ ID NO: 6: Synthetic DNA
SEQ ID NO: 7: Synthetic DNA
SEQ ID NO: 8: Synthetic DNA
SEQ ID NO: 9: Synthetic peptide
SEQ ID NO: 10: Synthetic peptide

The invention claimed is:

1. A method of preparing an antibody-producing cell, which comprises the following steps:
   (a) transplanting metastatic cancer cells expressing a target antigen into a non-human animal;
   (b) allowing engraftment of the metastatic cancer cells in the non-human animal;
   (c) immunizing the non-human animal with the target antigen by administering the target antigen to said non-human animal; and
   (d) collecting antibody-producing cells from the immunized, non-human animal of step (c), wherein the antibody-producing cells produce antibodies against said target antigen.

2. The method according to claim 1, which further comprises the step of immortalizing the collected antibody-producing cell.

3. A method for preparing a hybridoma cell, which comprises the step of fusing the antibody-producing cell obtained in claim 1 with a myeloma cell.

4. A method for preparing an antibody, which comprises the following steps of:
   (a) transplanting metastatic cancer cells expressing a target antigen into a non-human animal;
   (b) allowing engraftment of the metastatic cancer cells in the non-human animal;
   (c) immunizing the non-human animal with the target antigen by administering the target antigen to said non-human animal; and
   (d) collecting serum from the immunized, non-human animal of step (c), wherein said serum comprises antibodies against said target antigen.

5. The method according to claim 4, wherein the metastatic cancer cells are metastatic breast cancer cells.

6. The method according to claim 4, wherein the target antigen is a membrane protein.

7. The method according to claim 4, wherein the metastatic cancer cells are transplanted into the mammary gland in step (a).

8. The method of claim 1, wherein the transplanting step comprises transplanting at least $0.1 \times 10^6$ metastatic cancer cells.

9. The method of claim 1, wherein the method does not include a booster step.

10. The method of claim 1, wherein the metastatic cancer cells have a high metastatic potential.

11. The method of claim 1, wherein the metastatic cancer cells are selected from the group consisting of MCF7, MCF7-14, MDA-MB231, MDA-MB361, MDA-MB435, HT-1080, HepG2, T-24, SW620, A549, SW480, and A375.

12. The method of claim 1, wherein the metastatic cancer cells are MCF7, MDA-MB231 or MCF7-14.

13. The method according to claim 1, wherein the metastatic cancer cells are transplanted in a cell suspension in an admixture with a scaffold material.

* * * * *